US006894189B2

(12) United States Patent
Senanayake et al.

(10) Patent No.: US 6,894,189 B2
(45) Date of Patent: *May 17, 2005

(54) METHODS OF PREPARING DIDESMETHYLSIBUTRAMINE AND OTHER SIBUTRAMINE DERIVATIVES

(75) Inventors: Chris Hugh Senanayake, Shrewsbury, MA (US); Zhengxu Han, Shrewsbury, MA (US); Dhileepkumar Krishnamurthy, Westborough, MA (US); Derek Pflum, Waltham, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/643,941

(22) Filed: Aug. 20, 2003

(65) Prior Publication Data

US 2004/0087660 A1 May 6, 2004

Related U.S. Application Data

(63) Continuation of application No. 10/120,503, filed on Apr. 12, 2002, now Pat. No. 6,610,887.
(60) Provisional application No. 60/283,371, filed on Apr. 13, 2001.

(51) Int. Cl.$^7$ ............... C07C 209/62; C07C 211/17; C07C 251/06
(52) U.S. Cl. ............... 564/248; 564/338; 564/415
(58) Field of Search ............... 564/248, 338, 564/415

(56) References Cited

U.S. PATENT DOCUMENTS

| | | | |
|---|---|---|---|
| 3,155,669 A | 11/1964 | Janssen et al. | |
| 3,155,670 A | 11/1964 | Janssen et al. | |
| 3,471,515 A | 10/1969 | Troxler et al. | |
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 3,960,891 A | 6/1976 | Malen et al. | |
| 4,008,719 A | 2/1977 | Theeuwes et al. | |
| 4,522,828 A | 6/1985 | Jeffery et al. | |
| 4,552,828 A | 11/1985 | Toya et al. | |
| 4,746,680 A | 5/1988 | Jeffery et al. | |
| 4,806,570 A | 2/1989 | Jeffery et al. | |
| 4,814,352 A | 3/1989 | Jeffery et al. | |
| 4,816,488 A | 3/1989 | Rees | |
| 4,871,774 A | 10/1989 | Rees | |
| 4,929,629 A | 5/1990 | Jeffery | |
| 4,939,175 A | 7/1990 | Ukai et al. | |
| 4,988,814 A | 1/1991 | Abou-Gharbia et al. | |
| 5,059,595 A | 10/1991 | Le Grazie | |
| 5,068,440 A | 11/1991 | Jeffery et al. | |
| 5,073,543 A | 12/1991 | Marshall et al. | |
| 5,104,899 A | 4/1992 | Young et al. | |
| 5,120,548 A | 6/1992 | McClelland et al. | |
| 5,250,534 A | 10/1993 | Bell et al. | |
| 5,354,556 A | 10/1994 | Sparks et al. | |
| 5,436,272 A | 7/1995 | Scheinbaum | |
| 5,459,164 A | 10/1995 | Vargas | |
| 5,552,429 A | 9/1996 | Wong et al. | |
| 5,591,767 A | 1/1997 | Mohr et al. | |
| 5,639,476 A | 6/1997 | Oshlack et al. | |
| 5,674,553 A | 10/1997 | Shinoda et al. | |
| 5,719,283 A | 2/1998 | Bell et al. | |
| 5,733,566 A | 3/1998 | Lewis | |
| 5,780,051 A | 7/1998 | Eswara et al. | |
| 5,795,880 A | 8/1998 | Svec et al. | |
| 6,046,242 A | 4/2000 | Emmelmann | |
| 6,127,363 A | 10/2000 | Doherty et al. | |
| 6,174,925 B1 | 1/2001 | Bailey et al. | |
| 6,610,887 B2 * | 8/2003 | Senanayake et al. ........ 564/248 |

FOREIGN PATENT DOCUMENTS

| | | |
|---|---|---|
| DE | 32 12 682 A1 | 10/1982 |
| EP | 0 035 597 | 9/1981 |
| EP | 0 781 561 A1 | 7/1997 |
| GB | 2098602 A | 11/1982 |
| WO | WO 88/06444 | 9/1988 |
| WO | WO 90/06110 | 6/1990 |
| WO | WO 94/00047 | 1/1994 |
| WO | WO 94/00114 | 1/1994 |
| WO | WO 94/28902 | 12/1994 |
| WO | WO 95/20949 | 8/1995 |
| WO | WO 95/21615 | 8/1995 |
| WO | WO 97/03675 | 2/1997 |
| WO | WO 97/20810 | 6/1997 |
| WO | WO 98/06722 | 2/1998 |
| WO | WO 98/11884 | 3/1998 |
| WO | WO 98/13033 | 4/1998 |
| WO | WO 98/13034 | 4/1998 |
| WO | WO 00/32182 | 11/1998 |
| WO | WO 99/33450 | 7/1999 |
| WO | WO 00/54765 | 9/2000 |
| WO | WO 00/56148 | 9/2000 |
| WO | WO 00/56149 | 9/2000 |
| WO | WO 00/56150 | 9/2000 |
| WO | WO 00/56151 | 9/2000 |

(Continued)

OTHER PUBLICATIONS

Baldessarini et al., *Life Sciences* 39: 1765–1777, (1986).
Buckett et al., "BTS 54 524–An Approach to Rapidly Acting Antidepressant," *New Concepts in Depression* 2: 167–172 (1988).

(Continued)

*Primary Examiner*—Brain Davis
(74) *Attorney, Agent, or Firm*—Jones Day

(57) ABSTRACT

This invention encompasses novel methods of preparing sibutramine and sibutramine derivatives, and stereomerically pure sibutramine derivatives in particular. Examples of sibutramine derivatives include, but are not limited to, sibutramine metabolites such as desmethylsibutramine and didesmethylsibutramine. The invention further encompasses novel compounds useful in the synthesis of sibutramine derivatives.

12 Claims, No Drawings

FOREIGN PATENT DOCUMENTS

| WO | WO 00/56306 | 9/2000 |
|---|---|---|
| WO | WO 00/56309 | 9/2000 |
| WO | WO 00/56314 | 9/2000 |
| WO | WO 00/56315 | 9/2000 |
| WO | WO 00/56318 | 9/2000 |
| WO | WO 00/56321 | 9/2000 |
| WO | WO 00/56322 | 9/2000 |

OTHER PUBLICATIONS

Bucket et al., "The Pharmacology of Sibutramine Hydrochloride (BTS 54 524), A New Antidepressant which induces Rapid Noradrenergic Down–Regulation", *Prog. Neuro–Psychopharmacol. & Biol. Psychiat.* 12: 575–584 (1988).

Buckett et al., "Sibutramine Hydrochloride," *Drugs of the Future* 13(8): 736–738 (1988).

Butler, D., *Facile Cycloalkylation of Arylacetonitriles in Dimethyl Sulfoxide*, J. Org. Chem., 36:1308–1309 (1971).

Cannone, P., et al., *Effet du Benzene Dans la Reaction de Grignard sur les Nitriles*, Tetrahedron Lett., 21:155–58 (1980).

Carstensen, J., *Drug Stability: Principles & Practice*, 2d. Ed., pp. 379–380, pp. 379–80, Marcel Dekker, NY, NY, (1995).

Castello, R.A., et al., *Discoloration of Tablets Containing Amines and Lactose*, Pharm. Sci. 51(2):106–108 (1962).

Cheetham, S.C., et al., $[^3H]$*Paroxetine Binding in Rat Frontal Cortex Strongly Correlates with $[^3H]$5–HT Uptake: Effect of Administration of Various Antidepressant Treatments*, Neuropharmacology (1993), 32(8), 737–743.

Cliffe et al., *(S)–N–tert–Butyl–3–(4–(2–methoxyphenyl)–piperazine–1–yl)–2–phenylpropanamide [(S)–WAY–100135]: A Selective Antagonist at Presynaptic and Postsynaptic 5–HT$_{1A}$ Receptors*, Med. Chem., 36:1509–1510 (1993).

*Diagnostic and Statistical Manual of Mental Disorders*, Fourth Ed., American Psychiatric Association, (1997).

*Diagnostic and Statistical Manual of Mental Disorders*, 3rd Ed., American Psychiatric Association (1981).

Dreshfield et al., *Enhancement of Fluoxetine–Dependent Increase of Extracellular Serotonin (5–HT) Levels by (−)–Pindolol, an Antagonist at 5–HT$_{1A}$ Receptors*, Neurochem. Res., 21(5):557–562 (1996).

Eliel, E.L., *Stereochemistry of Carbon Compounds* (McGraw–Hill, NY, 1962).

Evans et al., "*Prevelence of Alzheimer's Disease in a Community Population of Older Persons*," J.A.M.A. 262: 2551–2556 (1989).

Fuentes, J.et al., "Comparison of the apparent anti–depressant activity of (−) and (+) tranylpromine in an animal model", *Chemical Abstracts*, 85: 7, p. 31, No. 40768t (1976).

Goodman & Gilman, The Pharmacological Basis of Therapeutics, 362–373, 404 (9$^{th}$ ed. McGraw–Hill, 1996).

Gray et al., *The Involvement of the Opioidergic System in the Antinociceptiv Mechanism of Action of Antidepressant Compounds*, BR.J. Pharmacol., vol. 124, No. 4, (1998) pp 669–674.

Handbook of Pharmaceutical Excipients, 2$^{nd}$ ed., Wade and Willer eds., pp. 257–259 (1994).

Heal et al., *A Comparison of the Effects on Central 5–HT Function of Sibutramine Hydrochloride and Other Weight–Modifying Agents*, BR.J. Pharmacol. (1998), 125(2), 301–308.

Hillver et al., *(S)–5–Fluoro–8–hydroxy–2–(dipropylamino)tetralix: A Putative 5–HT$_{1A}$ Receptor Antagonist*, J. Med. Chem., 33:1541–44 (1990).

J. Med. Chem., vol. 36, No. 17, 2540 (1993).

*Introduction to Pharmaceutical Dosage Forms*, 4th ed., Lea & Febiger, Philadelphia (1985).

Jacques et al., "Enantiomers, Racemates and Resolutions," (Wiley–Interscience, NY, 1981).

Jamali et al., *Journal of Pharmaceutical Sciences*, 78: 9: 695–715 (1989).

Jeffery et al., *Synthesis of Sibutramine, A Novel Cyclobutylalkylamine Useful in the Treatment of Obesity, and its Major Human Metabolites*, J. Chem. Soc. Perkin. Trans. 1, 2583–2589 (1996).

King et al., "Clinical Pharmacology of Sibutramine Hydrochloride (BTS 54524) A New Antidepressant, in Healthy Volunteers," *Clinical Pharmac.* 26: 607–611 (1989).

Kula et al., "*Effects of N–Substituted Phenyltetrahydropyridines on Cerebral High–Affinity Synatosomal Uptake of Dopamine and Other Monoamines in Several Mammalian Species,*" Life Sciences 34(26): 2567–2575, (1984).

Luscombe et al., *The Contribution of Metabolites to the Rapid and Potent Down–Regulation of Rat Cortical β–Adrenoceptors by the Putative Antidepressant Sibutramine Hydrochloride*, Neuropharmacology, vol. 28, No. 2, (1989) pp 129–134.

The Merck Manual of Diagnosis and Therapy, ??th Ed., Merck & Co., Inc., Whitehouse Station, NJ, (1999).

Middlemiss et al., *Centrally Active 5–HT Receptor Agonists and Antagonists*, Neurosci. and Biobehv. Rev., 16:75–82 (1992).

Moreau et al., *Behavioral Profile of the 5–HT$_{1A}$ Receptor Antagonist (S)–UH–301 in Rodents and Monkeys*, Brain Res. Bull., 29;901–04 (1992).

Nakada et al., *An Enantioconvergent Route to (−)–Kainic Acid*, Tetrahedron Lett., 38:857–860 (1997).

*Physician's Desk Reference®* 473–475 (53$^{rd}$ ed., 1999).
*Physician's Desk Reference®* 475–476 (53$^{rd}$ ed., 1999).
*Physician's Desk Reference®* 764–766 (53$^{rd}$ ed., 1999).
*Physician's Desk Reference®* 823–825 (53$^{rd}$ ed., 1999).
*Physician's Desk Reference®* 978–979 (53$^{rd}$ ed., 1999).
*Physician's Desk Reference®* 1054–1056 (53$^{rd}$ ed., 1999).
*Physician's Desk Reference®* 1332–1334 (53$^{rd}$ ed., 1999).
*Physician's Desk Reference®* 1369–1370 (53$^{rd}$ ed., 1999).
*Physician's Desk Reference®* 1432–1436 (53$^{rd}$ ed., 1999).
*Physician's Desk Reference®* 1494–1498 (53$^{rd}$ ed., 1999).
*Physician's Desk Reference®* 1641–1645 (53$^{rd}$ ed., 1999).
*Physician's Desk Reference®* 2004–2009 (53$^{rd}$ ed., 1999).
*Physician's Desk Reference®* 2075–2078 (53$^{rd}$ ed., 1999).
*Physician's Desk Reference®* 2190–2192 (53$^{rd}$ ed., 1999).
*Physician's Desk Reference®* 2367–2368 (53$^{rd}$ ed., 1999).
*Physician's Desk Reference®* 2396–2399 (53$^{rd}$ ed., 1999).
*Physician's Desk Reference®* 2490–2493 (53$^{rd}$ ed., 1999).
*Physician's Desk Reference®* 2516–2521 (53$^{rd}$ ed., 1999).
*Physician's Desk Reference®* 2688–2691 (53$^{rd}$ ed., 1999).
*Physician's Desk Reference®* 2701–2704 (53$^{rd}$ ed., 1999).
*Physician's Desk Reference®* 2720–2726 (53$^{rd}$ ed., 1999).
*Physician's Desk Reference®* 2735–2736 (53$^{rd}$ ed., 1999).
*Physician's Desk Reference®* 2886–2888 (53$^{rd}$ ed., 1999).

*Physician's Desk Reference®* 2908–2910 (53$^{rd}$ ed., 1999).
*Physician's Desk Reference®* 3092–3094 (53$^{rd}$ ed., 1999).
*Physician's Desk Reference®* 3101–3104 (53$^{rd}$ ed., 1999).
*Physician's Desk Reference®* 3224–3225 (53$^{rd}$ ed., 1999).
*Physician's Desk Reference®* 3267–3272 (53$^{rd}$ ed., 1999).
*Physician's Desk Reference®* 3307–3309 (53$^{rd}$ ed., 1999).
*Physician's Desk Reference®* 3383–3384 (53$^{rd}$ ed., 1999).
*Physician's Desk Reference®* 2520 (52$^{nd}$ ed., 1998).
*Physician's Desk Reference®* 2958 (52$^{nd}$ ed., 1998).
*Remingtons: The Practice of TheScience and Pharmacy*, 19$^{th}$ ed., Gennaro, ed., p. 1625 (1995).
*Remington's Pharmaceutical Sciences*, 18th ed., Mack Publishing, Easton PA (1990).
*Remington's Pharmaceutical Sciences*, 16th ed., Mack Publishing, Easton PA (1980).

Stock, M.J., *Sibutramine: A Review of the Pharmacology of a Novel Anti–Obesity Agent*, Int'l J. Obesity, 21(Supp. 1):S25–S29 (1997).

U.S. Pharmacopia (USP) SP (XXI)/NF (XVI).

Wilen et al., *Tetrahedron*, 2725–36 33(21) (1977).

Wilen, S.H., *Tables of Resolving Agents and Optical Resolutions* 268(E.L. Eliel ed., Univ. of Notre Dame Press, Notre Dame, IN, 1972).

* cited by examiner

METHODS OF PREPARING DIDESMETHYLSIBUTRAMINE AND OTHER SIBUTRAMINE DERIVATIVES

This application is a continuation of U.S. application Ser. No. 10/120,503, filed Apr. 12, 2002, now U.S. Pat. No. 6,610,887. This application claims priority to U.S. Provisional Application No. 60/283,371, filed Apr. 13, 2001, the entirety fo which is incorporated herein by reference.

1. FIELD OF THE INVENTION

This invention relates to methods of synthesizing sibutramine derivatives, which include sibutramine metabolites such as, but not limited to, desmethylsibutramine and didesmethylsibutramine.

2. BACKGROUND OF THE INVENTION

Sibutramine is a neuronal monoamine reuptake inhibitor, which has the chemical name [N-1-[1-(4-chlorophenyl)cyclobutyl]-3-methylbutyl]-N,N-dimethylamine. Originally disclosed in U.S. Pat. Nos. 4,746,680 and 4,806,570, sibutramine inhibits the reuptake of norepinephrine and, to a lesser extent, serotonin and dopamine. See, e.g., Buckett et al., *Prog. Neuro-psychopharm. & Biol. Psychiat.*, 12:575–584, 1988; King et al., *J. Clin. Pharm.*, 26:607–611 (1989).

Racemic sibutramine is sold as a hydrochloride monohydrate under the trade name MERIDIA®, and is indicated for the treatment of obesity. *Physician's Desk Reference®* 1509–1513 (54$^{th}$ ed., 2000). The treatment of obesity using racemic sibutramine is disclosed, for example, in U.S. Pat. No. 5,436,272.

Sibutramine is rapidly absorbed from the gastrointestinal tract following oral administration and undergoes an extensive first-pass metabolism that yields the metabolites desmethylsibutramine ("DMS") and didesmethylsibutramine ("DDMS"), as shown below in Scheme I.

Both didesmethylsibutramine and desmethylsibutramine have interesting and useful biological properties. Each of these sibutramine metabolites can exist as an enantiomeric pair of R and S enantiomers, as shown below in Scheme II, which also exhibit interesting and useful biological properties:

Scheme II

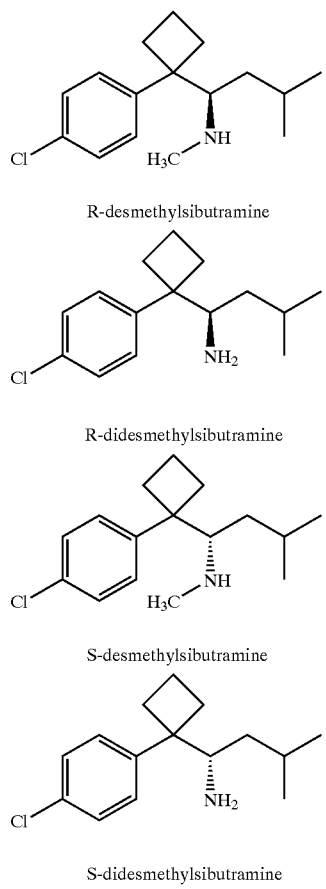

R-desmethylsibutramine

R-didesmethylsibutramine

S-desmethylsibutramine

S-didesmethylsibutramine

Scheme I

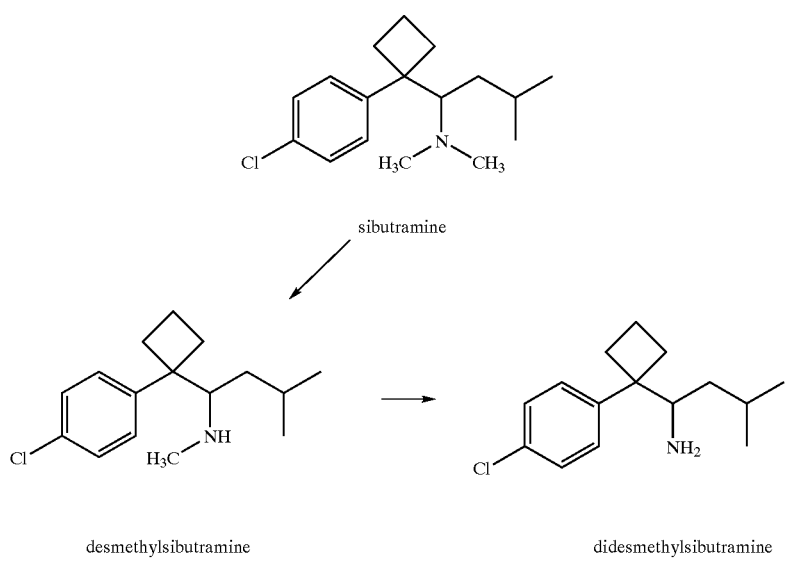

sibutramine desmethylsibutramine → didesmethylsibutramine

Until now, the preparation of racemic desmethylsibutramine and didesmethylsibutramine has been inefficient. Consequently, a need exists for improved methods of their synthesis. A particular need exists for the preparation of enantiomerically pure metabolites of sibutramine and derivatives thereof.

3. SUMMARY OF THE INVENTION

This invention is directed, in part, to novel methods of preparing sibutramine derivatives, and stereomerically (e.g., enantiomerically) pure sibutramine derivatives in particular. Examples of sibutramine derivatives include sibutramine metabolites such as, but are not limited to, desmethylsibutramine and didesmethylsibutramine. These derivatives, which can be made by the processes of the invention, are useful as pharmaceuticals or veterinary medicines and the like.

The invention also encompasses compounds useful in the preparation of sibutramine derivatives.

3.1. Definitions

As used herein, the term "prodrug" means a derivative of a compound that can hydrolyze, oxidize, or otherwise react under biological conditions (in vitro or in vivo) to provide the compound. Examples of prodrugs include, but are not limited to, derivatives of 2-(2-pyridylmethyl)sulfinyl) benzimidazoles that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of 2-(2-pyridylmethyl)sulfinyl)benzimidazoles that comprise —NO, —$NO_2$, —ONO, and —$ONO_2$ moieties.

As used herein, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "biohydrolyzable ester" means an ester of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable esters include, but are not limited to, lower alkyl esters, acyl esters (e.g., —C(O)Z, wherein Z is F, C, Br, I), alkoxyacyloxy esters, alkyl acylamino alkyl esters, and choline esters.

As used herein, the term "biohydrolyzable amide" means an amide of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable amides include, but are not limited to, lower alkyl amides, α-amino acid amides, alkoxyacyl amides, substituted and unsubstituted ureas, and alkylaminoalkylcarbonyl amides.

As used herein, the term "pharmaceutically acceptable salt" refers to a salt prepared from a pharmaceutically acceptable non-toxic inorganic or organic acid. Suitable non-toxic acids include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. For example, specific pharmaceutically acceptable salts are hydrochloride, maleic acid, and tartaric acid salts.

As used herein and unless otherwise indicated, the term "alkyl" includes saturated linear, branched, and cyclic hydrocarbon radicals having 1 to 20 carbon atoms, 1 to 12, 1 to 8, or 1 to 4 carbon atoms. An alkyl group can include one or more double or triple bonds or can be substituted with one or more heteroatoms or halogens (e.g., F, Cl, Br, I). It is understood that cyclic alkyl groups comprise at least three carbon atoms. Specific examples of branched alkyl have one or two branches. Unsaturated alkyl have one or more double bonds and/or one or more triple bonds. Specific examples of unsaturated alkyl have one or two double bonds or one triple bond. Alkyl chains may be unsubstituted or substituted with from 1 to 4 substituents. Specific examples of substituted alkyl are mono-, di-, or trisubstituted alkyl. Specific examples of alkyl substituents include halo, haloalkyl, hydroxy, aryl (e.g., phenyl, tolyl, alkyloxphenyl, alkyloxycarbonylphenyl, halophenyl), heterocyclyl, and heteroaryl.

As used herein and unless otherwise indicated, the term "lower alkyl" means branched or linear alkyl having from 1 to 8 or from 1 to 4 carbon atoms. Examples include, but are not limited to, methyl, ethyl, propyl, isopropyl, isobutyl, and tertiary butyl.

As used herein and unless otherwise indicated, the term "heteroalkyl" means a saturated or unsaturated chain containing carbon and at least one heteroatom, wherein no two heteroatoms are adjacent. Heteroalkyl chains contain from 1 to 18, 1 to 12, 1 to 6, or 1 to 4 member atoms (carbon and heteroatoms) in the chain. Heteroalkyl chains may be straight or branched. Specific examples of branched heteroalkyl have one or two branches. Unsaturated heteroalkyl have one or more double bonds and/or one or more triple bonds. Specific examples of unsaturated heteroalkyl have one or two double bonds or one triple bond. Heteroalkyl chains may be unsubstituted or substituted with from 1 to about 4 substituents. Specific examples of heteroalkyl are substituted or unsubstituted. Specific examples of heteroalkyl substituents include halo, hydroxy, aryl (e.g., phenyl, tolyl, alkyloxphenyl, alkyloxycarbonylphenyl, halophenyl), heterocyclyl, and heteroaryl. For example, alkyl substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di-$C_1$–$C_3$ alkanylamino, methylphenylamino, methylbenzylamino, $C_1$–$C_3$ alkanylamido, carbamamido, ureido, guanidino).

As used herein and unless otherwise indicated, the term "heteroatom" includes a nitrogen, sulfur, oxygen, or phosphorus atom. Groups containing more than one heteroatom may contain different heteroatoms.

As used herein and unless otherwise indicated, the term "aryl" includes an organic radical derived from an aromatic hydrocarbon by removal of one hydrogen, such as phenyl or naphthyl. Aryl rings are monocyclic or fused bicyclic ring systems. Monocyclic aromatic rings contain from about 5 to about 10 carbon atoms, from 5 to 7 carbon atoms, or from 5 to 6 carbon atoms in the ring. Bicyclic aromatic rings contain from 8 to 12 carbon atoms, or 9 or 10 carbon atoms in the ring. Aromatic rings may be unsubstituted or substituted with from 1 to about 4 substituents on the ring. Specific examples of aromatic ring substituents include: halo, cyano, alkyl, heteroalkyl, haloalkyl, phenyl, phenoxy or any combination thereof. More Specific examples of substituents include halo and haloalkyl. Specific examples of aromatic rings include naphthyl and phenyl.

As used herein and unless otherwise indicated, the term "aralkyl" means an aryl substituted with one or more linear, branched, or cyclic alkyl groups. Aralkyl moieties can be attached to other moieties through their aryl or alkyl components.

As used herein and unless otherwise indicated, the term "ether" includes alkyl groups wherein at least one carbon atom has been replaced with an oxygen atom, and aralkyl groups wherein at least one non-aromatic carbon atom has been replaced with an oxygen atom.

As used herein and unless otherwise indicated, the terms "heterocyclic group" and "heterocycle" include aromatic and non-aromatic heterocyclic groups containing one or more heteroatoms each selected from O, S, N, or P. Non-aromatic heterocyclic groups include groups having only 3 atoms in their ring system, but aromatic heterocyclic groups (i.e., heteroaryl groups) must have at least 5 atoms in their ring system. Heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl, and an example of a 10 membered heterocyclic group is quinolinyl. Examples of non-aromatic heterocyclic groups include, but are not limited to, pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and substituted derivative thereof. Examples of aromatic heterocyclic groups include, but are not limited to, pyridinyl, methylpyridine analgoues, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzoimidazoles, benzofuranyl, cinnolinyl, indazolyl, indolinyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and substituted derivatives thereof. The foregoing groups, as derived from the compounds listed above, may be C-attached or N-attached where such attachment is possible. For instance, a group derived from benzimidazol can be benzimidazol-1-yl (N-attached) or benzimidazol-2-yl (C-attached).

As used herein and unless otherwise indicated, the term "heteroaryl" means an aromatic heterocycle. A heteroaryl is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10, from 5 to 7, or from 5 to 6 member atoms (carbon and heteroatoms). Bicyclic heteroaromatic rings contain from 8 to 12 9 or 10 member atoms. Heteroaromatic rings may be unsubstituted or substituted with from 1 to about 4 substituents on the ring. Specific examples of heteroaromatic ring substituents include: halo, cyano, alkyl, heteroalkyl, haloalkyl, phenyl, phenoxy or any combination thereof. More Specific examples of substituents include halo, haloalkyl, and phenyl. Specific examples of heteroaromatic rings include thienyl, thiazolo, purinyl, pyrimidyl, pyridyl, and furanyl.

As used herein and unless otherwise indicated, the term "sulfide" includes alkyl groups wherein at least one carbon atom has been replaced with a sulfur atom, and aralkyl groups wherein at least one non-aromatic carbon atom has been replaced with a sulfur atom.

As used herein and unless otherwise indicated, the term "substituted" as used to describe a compound or chemical moiety means that at least one hydrogen atom of that compound or chemical moiety is replaced with a second chemical moiety. Examples of second chemical moieties include, but are not limited to: halogen atoms (e.g., chlorine, bromine, and iodine); $C_1$–$C_6$ linear, branched, or cyclic alkyl (e.g., methyl, ethyl, butyl, tert-butyl, and cyclobutyl); hydroxyl; thiols; carboxylic acids; esters, amides, silanes, nitriles, thioethers, stannanes, and primary, secondary, and tertiary amines (e.g., —$NH_2$, —$NH(CH_3)$, —$N(CH_3)_2$, and cyclic amines). Specific examples of second chemical moieties are chlorine, hydroxyl, methoxy, amine, thiol, and carboxylic acid.

As used herein and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diasteroemers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein and unless otherwise indicated, the term "polymer bound" and "polymer bound alkyl or aryl" mean that the compound of the invention is covalently bound to a polymer support, such as, but not limited to, Merrifield Resin, See Wang et al., *J. Org. Chem*, 1977, 42, 1286–1290; Wang Resin, See Fancelli et al., *Tetrahedron Lett.*, 1997, 38, 2311–2314; Aminomethyl Resin; MBHA Resin; Amino Acid-2-Chlorotrityl Resin; Carboxypolystyrene; 4-Nitrophenyl Carbonate Resin; Oxime Resin; Safety-Catch Resin; Alkenyl based resins; Br, Cl functionalized resins; Carbonate resins; CHO functionalized resins; $CO_2H$ functionalized resins; Diazonium-based resins; Enol functionalized resins; $NH_2$, $NH_2NH$ functionalized resins; OH functionalized resins; Orthogonal photocleavable resins; SH functionalized resins; Silylalkyl resins; Silyloxy resins; Triazene-based resins; Polymer-bound bases (e.g., (Polystyrylmethyl)trimethylammonium bicarbonate, Morpholinomethyl polystyrene HL, Piperazinomethyl polystyrene, Piperidine-4-carboxylic acid polyamine resin, Piperidinomethyl polystyrene, TBD-methyl polystyrene, Tris-(isonipecotylaminoethyl)-amine polystyrene); Polymer-bound coupling reagents (e.g., Ethoxycarbonylazocarboxymethyl polystyrene, HOBt-6-carboxamidomethyl polystyrene, N-Cyclohexylcarbodiimide,N'-methyl polystyrene); Polymer-bound oxidizing reagents (e.g., Polystyrylmethyl)trimethylammonium metaperiodate, (Polystyrylmethyl)trimethylammonium perruthenate, 4-(Polystyrylmethyloxy)-2,2,6,6-tetramethyl-piperidin-1-yloxy free radical, 6-(Methylsulfinyl)hexanoylmethyl polystyrene, TEMPO polystyrene); Polymer-bound phosphines (e.g., Di(n-butyl)phenylphosphine polystyrene, Di-o-tolylphenylphosphine polystyrene, Dicyclohexylphenylphosphine polystyrene, Diphenylphosphinobenzoyl NovaGel™ AM resin, Diphenylphosphinomethyl polystyrene, Diphenylphosphinopolystyrene, Triphenylphosphine NovaGel™, Triphenylphosphine polystyrene); or Polymer-bound reducing agents (e.g., (Polystyrylmethyl)trimethylammonium borohydride, (Polystyrylmethyl)trimethylammonium cyanoborohydride, Dimethylsilyl polystyrene).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4. DETAILED DESCRIPTION OF THE INVENTION

This invention is directed, in part, to novel methods of preparing sibutramine derivatives. The invention is directed in particular to methods of preparing racemic and enantiomerically pure sibutramine metabolites (e.g., desmethylsibutramine and didesmethylsibutramine), and racemic and enantiomerically pure compounds useful in such methods.

A first embodiment of the invention encompasses a method of preparing a compound of Formula 1:

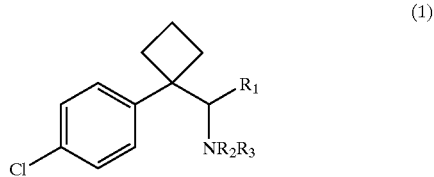

(1)

or a pharmaceutically acceptable salt, solvate, clathrate, hydrate, or prodrug thereof, wherein $R_1$ is substituted or unsubstituted alkyl, substituted or unsubstituted aralkyl, substituted or unsubstituted heteroalkyl, substituted or unsubstituted aryl, substituted or unsubstituted heterocycle; and $R_2$ and $R_3$ together form a cyclic structure (e.g., substituted or unsubstituted heterocycle or aryl) or each of $R_2$ and $R_3$ is independently substituted or unsubstituted alkyl, substituted or unsubstituted aralkyl, substituted or unsubstituted heteroalkyl, substituted or unsubstituted aryl, substituted or unsubstituted heterocycle;, which comprises contacting a compound of Formula 2:

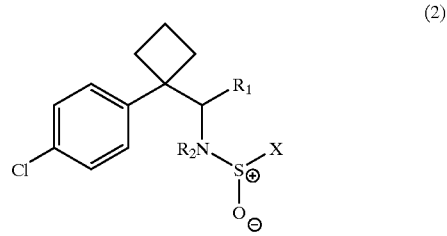

(2)

wherein X is independently a polymer bound alkyl, aryl or heteroalkyl; substituted or unsubstituted alkyl; substituted or unsubstituted aralkyl; substituted or unsubstituted heteroalkyl; substituted or unsubstituted aryl; substituted or unsubstituted ether; substituted or unsubstituted ester; substituted or unsubstituted ketone; substituted or unsubstituted phosphonate; substituted or unsubstituted phosphonic acid ester; substituted or unsubstituted phosphinoyl (e.g., —P(=O)($R_1$)$_3$, wherein $R_1$ is defined above), substituted or unsubstituted sulfide; substituted or unsubstituted sulfone; substituted or unsubstituted sulfinyl imine (e.g., —S(=O)(=N$R_1$)—$R_2$ wherein $R_1$ and $R_2$ are defined above); substituted or unsubstituted heterocycle; or —N$R_4R_5$, wherein $R_4$ and $R_5$ together with the nitrogen atom to which they are attached form a heterocycle or each of $R_4$ and $R_5$ is independently hydrogen, substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, or substituted or unsubstituted heterocycle; with a reagent capable of cleaving a nitrogen-sulfur bond under conditions suitable for the formation of the compound of Formula 1.

In a preferred method, the compounds of formulas 1 and 2 are stereomerically pure.

In another preferred method, the compound of Formula 1 is provided as a pharmaceutically acceptable salt. Examples of preferred pharmaceutically acceptable salts include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic salts.

In another preferred method of this embodiment, $R_1$ is lower alkyl, optionally substituted with one or more hydroxyl groups. Particularly preferred $R_1$ moieties are —$CH_2CH(CH_3)(CH_2OR_4)$, —$CH(OCH_2OCH_3)CH(CH_3)_2$, —$CH_2CH(CH_3)_2$, —$CH_2C(CH_3)_2OR_4$, and —$CH_2C(OR_4)(CH_2OR_4)CH_3$, wherein $R_4$ is alkyl, aryl, H, acyl, carbonates, carbamates, and ureas.

In another method, $R_2$ is not the same as $R_3$. In still another method of this embodiment, $R_2$ and $R_3$ are both hydrogen.

In another preferred method of this embodiment, X is alkyl, more preferably branched alkyl, examples of which include, but are not limited to, iso-propyl, iso-butyl, tertbutyl, adamantyl, 2-methylbutyl, triethylmethyl, and —$C(CH_3)_2C(CH_3)_3$. In another method, X is substituted or unsubstituted aryl, examples of which include, but are not limited to, phenyl, napthyl, substituted napthyl, 1,3,5-trimethylphenyl, 4-methylphenyl, 2-methoxyphenyl, 2-methoxynapthyl, and halogenated phenyl (e.g., 1-fluorophenyl, difluorophenyl, dichlorophenyl, hexaalkylphenyl, pentaalkylphenyl, trialkylphenyl, and dialkylphenyl).

In another preferred method, the reagent capable of cleaving a nitrogen-sulfur bond is an acid. A preferred acid is HCl.

The compound of Formula 2 can be prepared by contacting a compound of Formula 3:

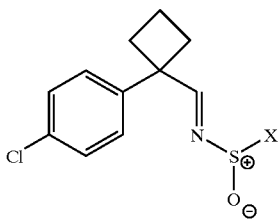
(3)

wherein X is described above, with a Lewis acid or a base and a compound of the formula $R_1M$, wherein M is Al, Ba, Li, Na, K, Ti, Mg, Mn, Zn, Cd, In, Cu, or is of the formula CdZ', BaZ', MgZ', ZnZ', AlZ'$_2$, MnZ', InZ', or CuZ', Ti(OR$_1$)$_3$Z', Ti(OR$_1$)$_4$, wherein Z'is Cl, Br, I, aryl, alkyl, heteroalkyl, aralkyl, or heterocycle and $R_1$ is described above under conditions suitable for the formation of the compound of Formula 2.

Examples of Lewis acids include, but are not limited to, $BF_3OEt_2$, $SnCl_4$, $Sc(OTf)_2$, $Al(alkyl)_3$, $Ti(alkyl)_4$, $Ti(alkoxy)_4$, $TiCl_4$, $Zn(OTf)_2$, $Mg(OTf)_2$, $TiHal_k(O-i-Pr)_{4-k}$ (where Hal is F, Cl, Br, or I, and k is 1, 2, or 3), and derivatives thereof. Specific compounds of the formula $R_1M$ include, but are not limited to:

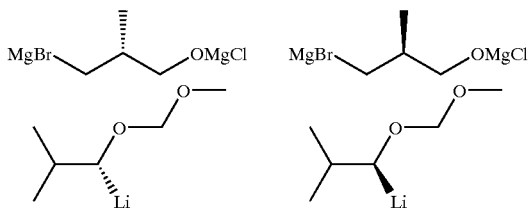

The compound of Formula 3 can be prepared by contacting a compound of Formula 4:

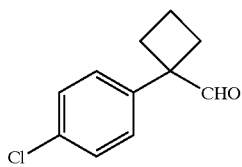
(4)

with a compound of Formula 5:

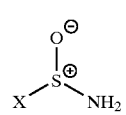
(5)

wherein X is defined above, under conditions suitable for the formation of the compound of Formula 3.

In a preferred method, the compound of Formula 5 is stereomerically pure, as shown below:

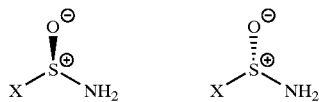

In another preferred method, the compound of Formula 5 is (R)-tert-butylsulfinamide, (S)-tert-butylsulfinamide, (R)-triethylmethylsulfinamide, or (S)-triethylmethylsulfinamide.

Examples of conditions suitable for the formation of the compound of Formula 3 include the presence of Ti(alkoxy)$_4$ (e.g., Ti(OEt)$_4$ and Ti(O-i-Pr)$_4$), TiHal$_k$(O-i-Pr)$_{4-k}$ (wherein Hal is F, Cl, Br, or I, and k is 1, 2, or 3), SnCl$_4$, MgSO$_4$, CuSO$_4$, Na$_2$SO$_4$.

A second embodiment of the invention encompasses compounds of Formula 2:

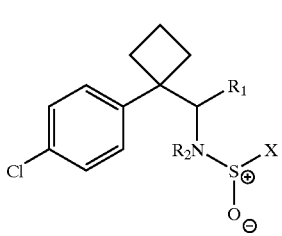
(2)

and salts, solvates, clathrates, hydrates, and prodrugs thereof, wherein each of X and $R_1$ is independently a polymer bound alkyl, aryl or heteroalkyl; substituted or unsubstituted alkyl; substituted or unsubstituted aralkyl; substituted or unsubstituted heteroalkyl; substituted or unsubstituted aryl; substituted or unsubstituted ether; substituted or unsubstituted ester; substituted or unsubstituted ketone; substituted or unsubstituted phosphonate; substituted or unsubstituted phosphonic acid ester; substituted or unsubstituted phosphinoyl (e.g., —P(=O)(R$_1$)$_3$, wherein $R_1$ is defined above), substituted or unsubstituted sulfide; substituted or unsubstituted sulfone; substituted or unsubstituted sulfinyl imine (e.g., —S(=O)(=NR$_1$)—R$_2$ wherein $R_1$ and $R_2$ are defined above); substituted or unsubstituted heterocycle; or —NR$_4$R$_5$, wherein $R_4$ and $R_5$ together with the nitrogen atom to which they are attached form a heterocycle or each of $R_4$ and $R_5$ is independently hydrogen, substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, or substituted or unsubstituted heterocycle; and $R_2$ is H, substituted or unsubstituted alkyl, substituted or unsubstituted aralkyl, or substituted or unsubstituted aryl.

In preferred compounds of Formula 2, $R_1$ is lower alkyl, optionally substituted with one or more hydroxyl groups. Particularly preferred $R_1$ moieties include, but are not limited to, —$CH_2CH(CH_3)(CH_2OR_4)$, —$CH(OCH_2OCH_3)CH(CH_3)_2$, —$CH_2CH(CH_3)_2$, —$CH_2C(CH_3)_2OR_4$, and —$CH_2C(OR_4)(CH_2OR_4)CH_3$, wherein $R_4$ is alkyl, aryl, H, acyl, carbonates, carbamates, and ureas.

In other preferred compounds, X is alkyl, more preferably branched alkyl, examples of which include, but are not limited to, iso-propyl, iso-butyl, tert-butyl, adamantyl, dimethyladamantyl, 2-methylbutyl, triethylmethyl, and —$C(CH_3)_2C(CH_3)_3$. In another method, X is substituted or unsubstituted aryl, examples of which include, but are not limited to, phenyl, napthyl, 1,3,5-trimethylphenyl, 4-methylphenyl, 2-methoxyphenyl, 2-methoxynapthyl, and halogenated phenyl.

Preferred compounds of Formula 2 are stereomerically pure. Examples of such compounds include:

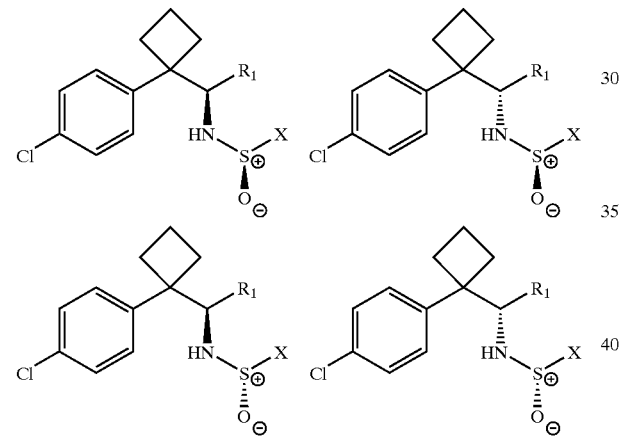

A third embodiment of the invention encompasses compounds of Formula 3:

(3)

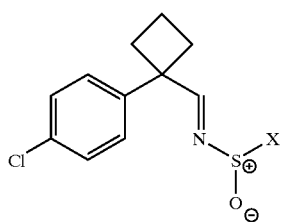

and salts, solvates, clathrates, hydrates, and prodrugs thereof, wherein X is independently a polymer bound alkyl, aryl or heteroalkyl; substituted or unsubstituted alkyl; substituted or unsubstituted aralkyl; substituted or unsubstituted heteroalkyl; substituted or unsubstituted aryl; substituted or unsubstituted ether; substituted or unsubstituted ester; substituted or unsubstituted ketone; substituted or unsubstituted phosphonate; substituted or unsubstituted phosphonic acid ester; substituted or unsubstituted phosphinoyl (e.g., —$P(=O)(R_1)_3$, wherein $R_1$ is defined above), substituted or unsubstituted sulfide; substituted or unsubstituted sulfone; substituted or unsubstituted sulfinyl imine (e.g., —$S(=O)(=NR_1)$—$R_2$ wherein $R_1$ and $R_2$ are defined above); substituted or unsubstituted heterocycle; or —$NR_4R_5$, wherein $R_4$ and $R_5$ together with the nitrogen atom to which they are attached form a heterocycle or each of $R_4$ and $R_5$ is independently hydrogen, substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, or substituted or unsubstituted heterocycle;

In preferred compounds of Formula 3, X is alkyl, more preferably branched alkyl, examples of which include, but are not limited to, iso-propyl, iso-butyl, tert-butyl, adamantyl, 2-methylbutyl, triethylmethyl, and —$C(CH_3)_2C(CH_3)_3$. In another method, X is substituted or unsubstituted aryl, examples of which include, but are not limited to, phenyl, napthyl, 1,3,5-trimethylphenyl, triisopropylphenyl, 4-methylphenyl, 2-methoxyphenyl, 2-methoxynapthyl, halogenated phenyl, and alkylphenyl including, but not limited to, di-, tri-, tetra-, and penta-alkylphenyls.

Preferred compounds of Formnula 3 are stereomerically pure. Examples of such compounds include:

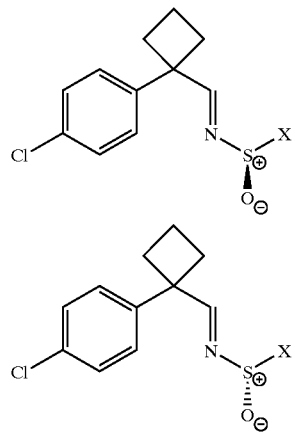

4.1. Preparation of Sibutramine Derivitives

Sibutramine, desmethylsibutramine, didesmethylsibutramine, and derivatives of each can be readily prepared according to the method shown below in Scheme III. This scheme, like others disclosed herein, is merely representative of a method of the invention, and is not to be construed as limiting its scope in any way.

Scheme III

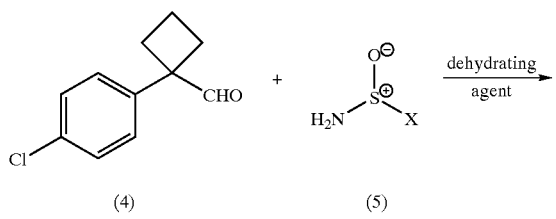

(4)   (5)

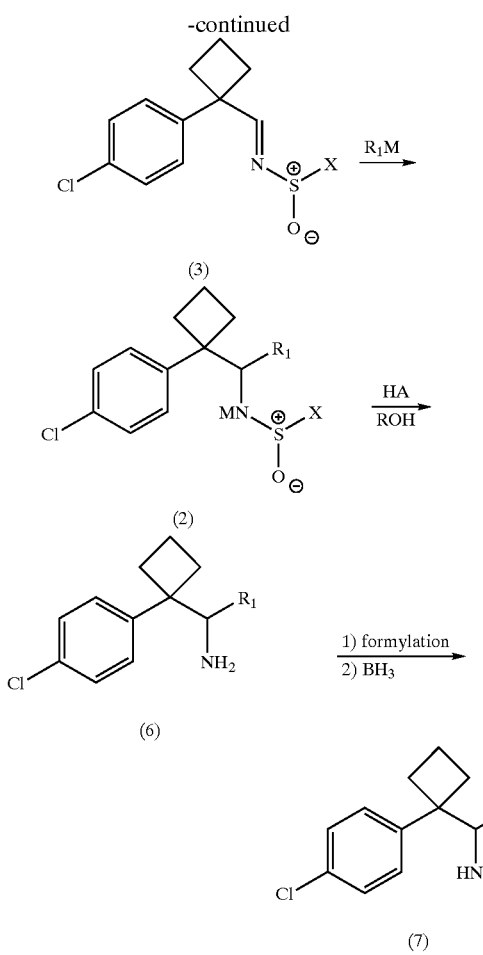

According to this method, 1-(4-chlorophenyl)-cyclobutanecarboxaldehyde (compound 4) is contacted with a sulfinamide of Formula 5 under reaction conditions suitable for the formation of compound 3. The compound of Formula 4 can be prepared by, for example, reducing 1-(4-chlorophenyl)-cyclobutane-carbonitrile with a suitable reductant such as, but not limited to, diisobutylaluminum hydride (DIBAL), Red-Al®, or Raney® nickel.

Sulfinamides of Formnula 5 can be prepared according to the methods known in the art or those disclosed by copending provisional U.S. patent application Ser. No. 60/283,337 to Senanayake et al., entitled "Methods of Preparing Sulfinamides and Sulfoxides" and filed Apr. 13, 2001, the entirety of which is incorporated herein by reference. Preferred sulfinamides are tert-butanesulfinamide (which is also referred to as "tert-butylsulfinamide") ("TBSA") and triethylmethyl sulfinamide.

The reaction of compounds 4 and 5 is preferably done in a solvent such as, but not limited to, toluene, THF, $CH_2Cl_2$, diethyl ether, MTBE, and mixtures thereof. The reaction is preferably catalyzed with a suitable dehydrating agent such as, but not limited to, $Ti(alkoxy)_4$ (e.g., $Ti(OEt)_4$ and $Ti(O\text{-}i\text{-}Pr)_4$), $TiHal_k(O\text{-}i\text{-}Pr)_{4-k}$ (wherein Hal is F, Cl, Br, or I, and k is 1, 2, or 3), $SnCl_4$, $MgSO_4$, $CuSO_4$, $Na_2SO_4$. Preferably, this reaction is run using a ratio of about 1 to about 4 equivalents of compound 4 to about 0.75 to about 1.5 equivalents of compound 5 and about 0.1 to about 10 equivalents dehydrating agent. The reaction can be run at a temperature of from about −20° C. to about 110° C., more preferably from about 0° C. to about 40° C., and most preferably from about 15° C. to about 25° C.

The imine of Formula 3 is then contacted with a compound of the formula $R_1M$ under conditions suitable for the formation of a compound of Formula 2, wherein $R_1$ is defined herein and M can be any metal or metal complex suitable for the reaction. Examples of M include, but are not limited to, CdZ, BaZ, Na, K, MgZ, ZnZ, Li, MnZ, CuZ, or In, and Z is Cl, Br, I, aryl, heteroalkyl, aralkyl, alkoxy, heteroaryl, or heterocycle under conditions suitable for the formation of the compound of Formula 2. $R_1M$ is preferably of the formula $(CH_3)_3CHCH_2Li$. Preferred compounds of the formula $R_1M$ described herein can be made by methods known in the art. See, e.g., Jeffery, J. E., et al., *J. Chem. Soc. Perkins. Trans. 1*, (1996) 2583–2589; Chan, P. C.-M. and Chong, J. M., *J. Org. Chem.* (1988) 53:5586–5588.

The reaction of the compound of Formnula 3 with $R_1M$ is preferably done at a temperature of from about −78° C. to about 10° C., more preferably from about −78° C. to about 25° C., and most preferably from about −78° C. to about 0° C. The reaction is preferably done in the presence of from about 1 to about 4 equivalents of a Lewis acid ("HA") or a base. Preferred Lewis acids are $BF_3.OEt_2$ and $Al(alkyl)_3$, although a variety of others will be apparent to those of skill in the art. The effects each can have on the synthesis of enantiomerically enriched (e.g., enantiomerically pure) didesmethylsibutramine is shown below in Table 1:

TABLE 1

The Synthesis of Didesmethylsibutramine Using an Imine of (R)-TBSA with i-BuLi as Organometallic Reagent

| Lewis acid or Lewis base (equivalents) | Solvent/Temperature | Yield | ee |
|---|---|---|---|
| $BF_3.OEt_2$ (2.2) | THF/−78° C. | 85% | (R)-98.8% |
| none | THF/−78° C. | 60% | (R)-98.3% |
| $BF_3.OEt_2$ (2.2) | THF/0° C. | 62% | (R)-84% |
| $BF_3.OEt_2$ (2.2) | THF/−20° C. | 66% | (R)-91% |
| none | THF/−20° C. | 40% | (R)-88% |
| $BF_3.OEt_2$ (0.2) | THF/−20° C. | 60% | (R)-90.5% |
| none | THF/−45° C. | 73% | (R)-96% |
| $AlMe_3$ (1.2) | THF/−78° C. | 90% | (R)-98.7% |
| $AlMe_3$ (1.2) | THF/−20° C. | 71% | (R)-88% |
| $Al(Oct)_3$ (1.2) | THF/Toluene/−78° C. | 85% | (R)-98% |
| TMEDA (2.2) | Toluene/−78° C. | 84% | (R)-98.7% |
| TMEDA (2.2) | Toluene/−20° C. | 53% | (R)-93.7% |
| $BF_3.OEt_2$ (2.2) | Toluene/−78° C. | 72% | (R)-98% |
| $BF_3.OEt_2$ (1.2) | Toluene/−78° C. | 73% | (R)-97% |
| none | Toluene/−78° C. to 0° C. | 74% | (R)-66% |
| $BF_3.OEt_2$ (2.2) | Toluene/−45° C. | 75% | (R)-92% |
| $BF_3.OEt_2$ (2.2) | Toluene/−20° C. | 76% | (R)-83% |
| $BF_3.OEt_2$ (1.2) | Toluene/−20° C. | 80% | (R)-55.5% |
| $BF_3.OEt_2$ (2.2) | Toluene/−0° C. | 75% | (R)-57% |
| none | Toluene/−20° C. | 76% | (R)-44% |
| $AlMe_3$ (1.2) | Toluene/−78° C. | No reaction | |
| $AlMe_3$ (1.2) | Toluene/−45° C. | 36% | (S)-38% |
| $Al(Oct)_3$ (1.2) | Toluene/−78° C. | No reaction | |
| $Al(Oct)_3$ (1.2) | Toluene/−20° C. | 37% | (S)-76% |

Finally, as shown in Scheme III, the sulfinyl group is removed from compound 2 to afford compound 6, preferably using from about 1 to about 10 equivalents of a dilute acid, although other reaction conditions known in the art can also be used. The removal of the sulfinyl group is preferably done at a temperature of from about 0° C. to about 150° C., more preferably from about 50° C. to about 125° C., and most preferably from about 100° C. to about 115° C. Compound 6, which is a primary amine, can be purified and isolated as a free base or as a salt by known methods.

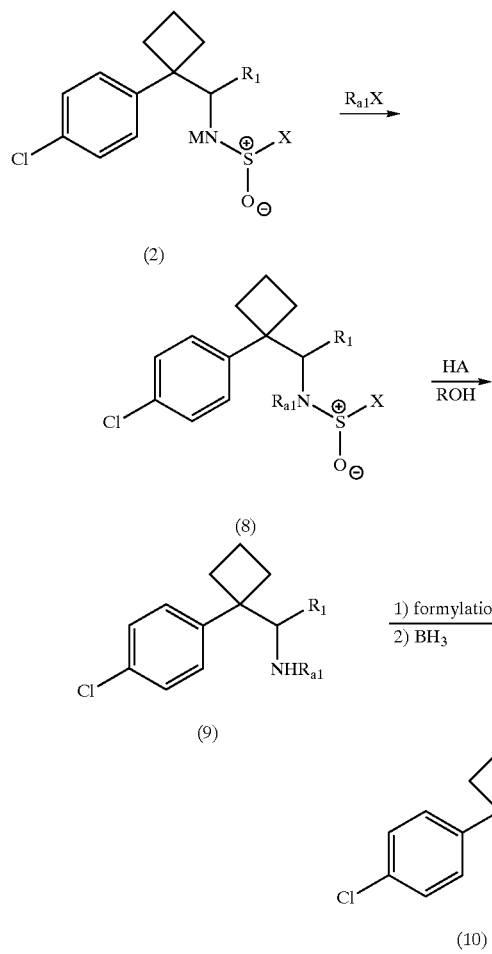

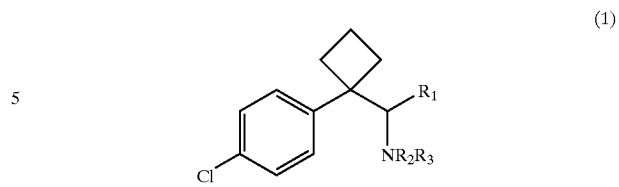

wherein $R_2$ and $R_3$ are defined herein. For example, if $R_1$ is —$CH_2CH(CH_3)_2$ and $R_2$ and $R_3$ are both hydrogen, the compound of Formula 6 is didesmethylsibutramine, which can be methylated to provide desmethylsibutramine ($R_2$=H; $R_3$=—$CH_3$), and methylated again to provide sibutramine ($R_2$=$R_3$=—$CH_3$).

In a preferred method encompassed by that shown above in Scheme III, a stereomerically pure sulfinamide of Formula 5 is used to provide enantiomerically pure sibutramine metabolites. For example, (R)-TBSA:

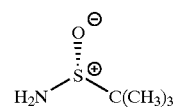

can be used to provide enantiomerically pure (R)-didesmethylsibutramine:

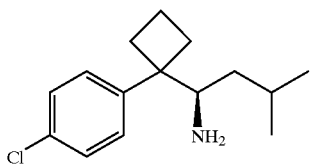

which can then be methylated to provide enantiomerically pure (R)-desmethylsibutramine.

The methylation of the compound of Formula 6 can be accomplished as shown in Scheme III by its formylation at a temperature of from about 0° C. to about 150° C., more preferably from about 50° C. to about 125° C., and most preferably from about 100° C. to about 115° C. using from about 1 to about 5 equivalents of formic acid. The resulting intermediate can then be contacted with, for example, from about 2 to about 5 equivalents $BH_3$ at a temperature of from about 0° C. to about 110° C., more preferably from about 20° C. to about 80° C., and most preferably from about 55° C. to about 75° C.

Whatever the final material is that is prepared according to the general, non-limiting, method represented by Scheme III, it can optionally be further purified, isolated, and/or resolved to obtain pure solid material, preferably crystalline material, which can then optionally be sterilized for use in GMP manufacturing or pharmaceutical formulation.

5. EXAMPLE

Asymmetric Synthesis of Didesmethylsibutramine

Preparation of (R)-N-(1-(4-chlorophenyl)-cyclobutylmethylidene-2-methyl propane sulfinamide: To a THF (25 mL) solution of 1-(4-chlorophenyl)-cyclobutane-carboxaldehyde (2.0 g, 10.4 mmol) at room temperature was added Ti(OEt)$_4$ (22.5 mL, about 20% in ethanol) and t-butylsulfinamide (1.2 g, 9.9 mmol). After stirring for 6–8 h, as monitored by TLC for the disappearance of t-butylsulfinamide, the reaction mixture was poured to brine In an alternative to Scheme III, Scheme IV describes the alkylation of a compound of formula 2, in situ, to form an N-alkyl sulfinamide of Formula 8. The procedure described above is generally followed to form the compound of Formula 2. The compound of Formula 2 is then contacted with a compound of the formula $R_{a1}X$ under conditions suitable for the formation of an N-alkyl sulfinamide of Formula 8, wherein $R_{a1}$ is a substituted or unsubstituted alkyl group and X is a halogen, for example, Cl, Br, or I, under conditions suitable for the formation of the compound of Formula 8. $R_{a1}X$ is preferably MeI.

Finally, as shown in Scheme IV, the sulfinyl group is removed from compound 8 to afford compound 9, preferably using from about 1 to about 10 equivalents of a dilute acid, although other reaction conditions known in the art can also be used. The removal of the sulfinyl group is preferably done at a temperature of from about 0° C. to about 150° C., more preferably from about 50° C. to about 125° C., and most preferably from about 100° C. to about 115° C. Compound 9, which is a secondary amine, can be purified and isolated as a free base or as a salt by known methods.

In an optional embodiment, the compound of Formula 9 can be formylated and reduced to afford a tertiary amine of Formula 10.

In another embodiment the amine group of compound 6, illustrated in Scheme 3, can also be alkylated by known methods to yield compounds of Formula 1:

(30 mL) at room temperature with stirring. The resulting suspension was filtered and filter cake was washed with EtOAc. The filtrate was then washed with brine, dried over Na$_2$SO$_4$ and evaporated to provide the crude sulfinimine product (2.9 g) with 98% yield (the product was used in the next step without purification). $^1$H NMR (CDCl$_3$): δ 1.24 (s, 9H), 1.87–2.20 (m, 2H), 2.45–2.90 (m, 4H), 7.08-7.46 (m, 4H), 8.07 (s, 1H). $^{13}$C NMR(CDCl$_3$): δ16.2, 22.6, 31.0, 31.4, 52.1, 57.3, 127.8, 128.9, 132.7, 142.7, 170.8.

Preparation of (R)-DDMS: In a 50 mL two-necked, round-bottomed flask equipped with a magnetic stir bar, temperature probe, rubber septum was charged imine (0.25 g, 0.84 mmol) and THF (3 mL) under Ar atmosphere. The reaction mixture was cooled to 0° C., BF$_3$.OEt$_2$ (0.24 g, 1.7 mmol) was added and the mixture was stirred for 30 min. Then the reaction mixture was cooled to −78° C., isobutyl lithium (0.8 mL, 2.0M in hexane) was added for 30 minutes, and the reaction monitored by TLC. The reaction was quenched with aqueous NH$_4$Cl (3 mL) and extracted with EtOAc (4 mL). The organic phase was treated with HCl in methanol (3 mL, 4M) and stirred at room temperature for 3 hours. The reaction mixture was neutralized with 2N NaOH to pH 8-9 and the organic phase was separated. The aqueous phase was extracted with EtOAc (3 mL) and the combined organic phases were washed with brine (5 mL), dried over Na$_2$SO$_4$ and evaporated under reduced pressure to provided the title compound (R)-DDMS with 98.8% ee and 85% yield (based on weight percent assay by HPLC. Column, symmetry C 18, 3.9 mm×150 mm; mobile phase, MeOH/H$_2$O (80/20, pH 7.0); flow rate, 1.0 mL/mm; wavelength, 220 nm.) (HPLC for analysis of DDMS enantiomeric purity, Ultron ES-OVM, 150 mm×4.6 mm; mobile phase, 0.01M KH$_2$PO$_4$/MeOH (70/30); flow rate, 1.0 m/min; wavelength, 220 nm; (R)-DDMS, r$_t$=4.6 min., (S)-DDMS, r$_t$=5.6 mm.)

Preparation of (R)-DDMS.D-TA salt: To the above crude product was added toluene (5 mL), the reaction mixture was heated to 55–60° C., and then D-TA (0.11 g, 0.73 mmol) in water and acetone (0.5 mL, 2:1, v/v) was added in 10 min. The reaction mixture was heated to reflux and the water was removed by Dean-stark trap until the internal reaction mixture temperature reached >95° C. The reaction mixture was cooled to 20° C., the slurry was filtered and the filter cake washed with MTBE. The wet cake was dried under reduced pressure at 40–45° C. to furnish (R)-DDMS.D-TA (0.25 g, 87%) of 99% ee (same HPLC condition was used for (R)-DDMS free base). $^1$H NMR(DMSO-d$_6$): δ 0.7–0.9 (m, 6H), 0.9–1.05 (t, 1H), 1.1–1.24 (b, 1H), 1.5–1.8 (b, 2H), 1.8–2.02 (b, 1H), 2.1–2.4 (3, 3H), 2.4–2.6 (b, 1H), 3.5 (m, 1H), 4.0 (s, 2H), 6.7–7.1 (6H from NH$_2$, OH, and COOH). $^{13}$C NMR: δ 15.4, 21.5, 22.0, 22.2, 32.0, 32.2, 38.4, 49.0, 54.0, 72.8, 128.8, 130.0, 132.0, 143.0, 175.5.

Preparation of (S)-DDMS and (S)-DDMS.L-TA: The same procedure described above for the preparation of (R)-DDMS. D-TA was used except (R)-TBSA and D-TA were replaced with (S)-TBSA and L-TA to provide (S)-DDMS.L-TA with 99% ee and 72% overall yield. $^1$H NMR (DMSO-d$_6$): δ 0.7–0.9 (m, 6H), 0.9–1.05 (m, 1H), 1.1–1.3 (b, 1H), 1.52–1.8 (b, 2H), 1.84–2.05 (b, 1H), 2.15–2.4 (b, 3H), 2.4–2.6 (b, 1H), 3.65–3.58 (m, 1H), 4.0 (s, 2H), 6.7–7.3 (b, 6H from NH$_2$, OH and COOH) 7.1–7.6 (m, 4H). $^{13}$C NMR: δ 15.4, 21.5, 22.0, 22.2, 32.0, 32.2, 38.4, 49.0, 54.0, 72.8, 128.8, 130.0, 132.0, 143.0, 175.5.

Preparation of (R)-DDMS.D-TA (one pot procedure): A 250 mL two-necked, round bottom flask equipped with a magnetic stir bar, temperature probe, and rubber septum was charged with (R)-N-(1-(4-chlorophenyl)-cyclobutylmethylidene)-t-butane sulfinamide (5.3 g, 17.8 mmol), THF (20 mL), and toluene (20 mL) under argon. The reaction mixture was cooled to 0° C. and BF$_3$.OEt$_2$ (2.53 g, 17.8 mmol) was added, and the mixture was stirred for 30 minutes. The reaction mixture was then cooled to −45° C.–−50° C., and i-BuLi (23.8 mL, 1.5 M in hexane) was added dropwise over 2–3 hours, and the reaction was monitored by TLC. The reaction was quenched by the slow addition of HCl/MeOH (30 mL, 4 M), and the reaction mixture was warmed to room temperature and stirred for 1 hour. Aqueous NaOH (approx. 30 mL, 5M) was added to bring the pH of the reaction mixture to greater than 9, and the organic phase was separated. The aqueous phase was extracted with toluene (20 mL) and EtOAc (20 mL). The combined organic phases were washed with brine (20 mL) and distilled until the internal temperature exceed 90° C. The mixture was the cooled to 70° C. and D-TA(2.95 g) in water (6 mL) and acetone (3 mL) was added over 10 minutes. The resulting mixture was heated to reflux and the water was removed by Dean-stark trap until the internal temperature exceeded 100° C. The mixture was cooled to 20° C. and the resulting slurry was filtered, washed with MTBE (30 mL), and dried under reduced pressure to afford 5.8 g (81%) (R)-DDMS.D-TA with 98.4% ee and 99.6% chemical purity.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of preparing a compound of Formula 1:

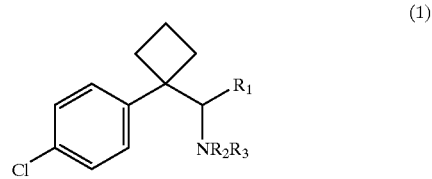

(1)

or a pharmaceutically acceptable salt, solvate, clatbrate, hydrate, or prodrug thereof, wherein R$_1$ is substituted or unsubstituted alkyl; and each R$_2$ and R$_3$ is independently hydrogen or substituted or unsubstituted alkyl, which comprises contacting a compound of Formula 2:

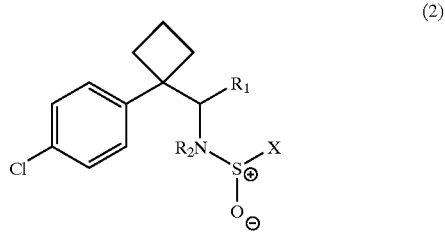

(2)

wherein X is independently a polymer bound alkyl, aryl or heteroalkyl; substituted or unsubstituted alkyl; substituted or unsubstituted aralkyl; substituted or unsubstituted heteroalkyl; substituted or unsubstituted aryl; substituted or unsubstituted ether; substituted or unsubstituted ester; substituted or unsubstituted ketone; substituted or unsubstituted phosphonate; substituted or unsubstituted phosphonic acid ester; substituted or unsubstituted phosphinoyl; substituted or unsubstituted sulfide; substituted or unsubstituted sulfone; substituted or unsubstituted sulfinyl imine; substituted or unsubstituted heterocycle; or $NR_4R_5$, wherein $R_4$ and $R_5$ together with the nitrogen atom to which they are attached form a heterocycle or each of $R_4$ and $R_5$ is independently hydrogen, substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, or substituted or unsubstituted heterocycle; with a reagent capable of cleaving a nitrogen-sulfur bond under conditions suitable for the formation of the compound of Formula 1.

2. The method of claim 1, wherein the compounds of formulas 1 and 2 are stereomerically pure.

3. The method of claim 1, wherein the compound of Formula 1 is provided as a pharmaceutically acceptable salt.

4. The method of claim 3, wherein the compound of Formula 1 is provided as an acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, or p-toluenesulfonic salt.

5. The method of claim 1, wherein $R_1$ is lower alkyl, optionally substituted with one or more hydroxyl groups.

6. The method of claim 5, wherein $R_1$ is $CH_2CH(CH_3)(CH_2OR_4)$, $CH(OCH_2OCH_3)CH(CH_3)_2$, $CH_2CH(CH_3)_2$, $CH_2C(CH_3)_2OR_4$, or $CH_2C(OR_4)(CH_2OR_4)CH_3$, wherein $R_4$ is alkyl, heteroalkyl, heteroaryl, aryl, hydrogen, acyl, carbonate, carbamate, ester, or urea.

7. The method of claim 1, wherein $R_2$ is not the same as $R_3$.

8. The method of claim 1, wherein $R_2$ and $R_3$ are both hydrogen.

9. The method of claim 1, wherein $R_2$ is methyl and $R_3$ is hydrogen.

10. The method of claim 1, wherein X is substituted or unsubstituted aralkyl, substituted or unsubstituted heterocycle, substituted or unsubstituted heteroalkyl, or substituted or unsubstituted heteroaryl.

11. The method of claim 1, wherein X is alkyl.

12. The method of claim 1, wherein x is aryl.

* * * * *